United States Patent [19]

Salari et al.

[11] Patent Number: 5,506,217
[45] Date of Patent: Apr. 9, 1996

[54] PHOSPHONATES AS ANTI-CANCER AGENTS

[75] Inventors: Hassan Salari, Ladner, Canada; Robert Bittman, Roslyn Heights, N.Y.

[73] Assignee: The University of British Columbia, Vancouver, Canada

[21] Appl. No.: 337,958

[22] Filed: Nov. 10, 1994

Related U.S. Application Data

[63] Continuation-in-part of Ser. No. 59,170, May 4, 1993, Pat. No. 5,369,097, which is a continuation-in-part of Ser. No. 835,732, Feb. 11, 1992, Pat. No. 5,219,845, which is a continuation-in-part of Ser. No. 692,452, Apr. 25, 1991, abandoned.

[51] Int. Cl.$^6$ ................................. A61K 31/685
[52] U.S. Cl. ............................. 514/77; 558/169
[58] Field of Search ................................. 514/77

[56] References Cited

U.S. PATENT DOCUMENTS

| | | | |
|---|---|---|---|
| 4,408,052 | 10/1983 | Hozumi et al. | 546/22 |
| 4,515,722 | 5/1985 | Yang et al. | 554/79 |
| 5,219,845 | 6/1993 | Salari et al. | 514/77 |
| 5,369,097 | 11/1994 | Salari et al. | 514/77 |

FOREIGN PATENT DOCUMENTS

| | | |
|---|---|---|
| 1240534 | 1/1989 | Canada . |
| 0108565 | 5/1984 | European Pat. Off. . |
| 0230575 | 4/1986 | European Pat. Off. . |
| 0338407 | 10/1989 | European Pat. Off. . |
| 0092190 | 10/1993 | European Pat. Off. . |
| 60-69088 | 4/1985 | Japan . |

OTHER PUBLICATIONS

*Chemical Abstracts*, vol. 114, 1991, p. 767, Abstract No. 82129h; German Democratic Rep. 278,800.
Yuan, W. et al., "Phosphate–Containing Phospholipid Analogues as Tight–Binding Inhibitors of Phosphollipase–A$_2$," *J. Am. Chem. Soc.*, vol. 110 (1988), pp. 2665–2666.
Carter, S. K. et al., "Chemotherapy of Cancer," Second Edition; John Wiley and Sons; New York, 1981; Appendix C.
*Chemical Abstracts*, vol. 117 (1992), p. 794, Abstract No. 90393s; Ries, U. J. et al., "Synthesis of Alkylphosphonates, a New Class of Antineoplastic Agents," *Chem. Phys. Lipids*, vol. 61, No. 3 (1992), pp. 225–234.
*Chemical Abstracts*, vol. 103, No. 21 (1985), p. 701, Abstract No. 178451f; Japan Kokai Tokyo Koho 60–069088.

*Primary Examiner*—Johann Richter
*Assistant Examiner*—Michael G. Ambrose
*Attorney, Agent, or Firm*—Oyen Wiggs Green & Mutala

[57] ABSTRACT

This invention pertains to the synthesis and use as anticancer therapeutic agents of a group of substances with a glycerol backbone linked to phosphonocholine, or other phosphorus-containing head groups, of the following formula:

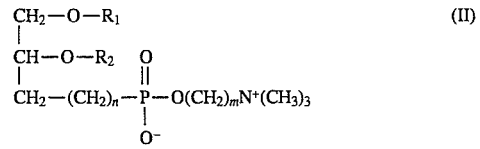

wherein n is 0 to 14 and $R_1$ is an alkyl group containing 12 to 20 carbon atoms, $R_2$ is a methyl group, n=0 to 14 and m=2 to 10, or enantiomer thereof, or mixture of stereoisomers. This invention also pertains to the following formula:

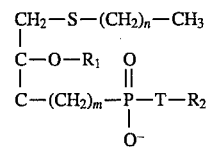

wherein n is 15 to 17; R1 is an alkyl group: m is 0 to 2; T is an oxygen atom or a methylene; and $R_2$ is a choline group and therapeutically effective pharmaceutically acceptable salts thereof. These thiophosphonolipids are useful for treating cancer in a mammal in need of cancer treatment.

51 Claims, No Drawings

PHOSPHONATES AS ANTI-CANCER AGENTS

This application is a continuation-in-part of application Ser. No. 08/059,170, filed May 4, 1993, now U.S. Pat. No. 5,369,091, which was a continuation-in-part of application Ser. No. 07/835,732, filed Feb. 11, 1992, now U.S. Pat. No. 5,219,845, which was a continuation-in-part of application Ser. No. 07/692,452, filed Apr. 25, 1991, abandoned

FIELD OF THE INVENTION

This invention pertains to the synthesis and use as anti-cancer therapeutic agents of a group of substances with a glycerol backbone linked to phosphonocholine or other phosphorus-containing head groups.

BACKGROUND OF THE INVENTION

European Patent No. P0230 575A2, dated Apr. 12, 1986, discloses a group of glyccrophospholipid compounds having an alkyl chain of C2-C22 and a methoxy group at the sn-2 position and a phosphocholine at the sn-3 position. These compounds are stated to be useful as anti-cancer agents.

U.S. Pat. No. 4,408,052, dated Feb. 25, 1981, assigned to Takeda Chemical Industries, Osaka. Japan, claims a group of phospholipid carbamates useful as antirumor agents.

Canadian Patent No. 1,248,534, dated Jan. 10, 1989, granted to Takeda Chemical Industries of Japan, protects a group of ketolyso phospholipids, which purportedly are useful as antitumor agents.

U.S. Pat. No. 4,515,722, dated May 7, 1985. granted to Merck Sharp & Dohme. protects a group of phosphatidylinositol analogs which are evidently effective in inhibiting phospholipase C and thereby have utility as anti-inflammatory and analgesic agents.

None of these patents discloses a substance with a glycerol backbone linked to a phosphorus atom with a polar head group useful as an anti-cancer therapeutic agent.

SUMMARY OF THE INVENTION

The present invention provides anti-cancer phospholipids of the general formula:

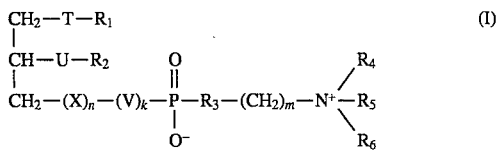

wherein T is an oxygen or sulphur atom: U is an oxygen atom or NH; $R_1$ is an aliphatic chain. containing 12 to 20 carbon atoms, such as hexadecyl or octadecyi; $R_2$ is a methyl group when U is oxygen, or sulphur when U is NH; X is a methylene group; n is 0 to 14; V is oxygen; k is 0 or 1; $R_3$ is either an oxygen atom or a methylene group; m is 2,3,4,5,6,7,8, or 9; and $R_4$, $R_5$ and $R_6$ represent alkyl groups containing 1 to 3 carbon atoms.

Phosphonate compounds of the general formula:

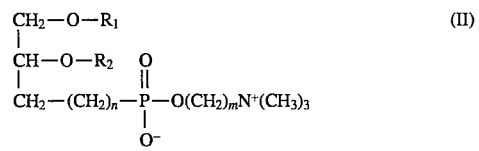

wherein $R_1$ is an alkyl group containing 12 to 20 carbon atoms, $R_2$ is a methyl group, n is 0 to 14 and m=2 to 10.

Phosphonate compounds of the general formula:

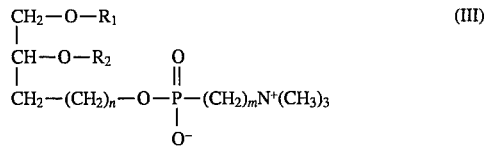

wherein $R_1$ is an alkyl group containing 12 to 20 carbon atoms, $R_2$ is a methyl group, n=0 or 1 and m=2–10.

A method of treating cancer in a mammal afflicted with cancer, comprising treating the afflicted mammal with a therapeutic amount of a phosphonate compound of the following general formula:

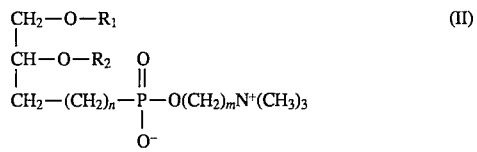

wherein, $R_1$ is an alkyl group containing 12 to 20 carbon atoms such as hexadecyl or octadecyl, $R_2$ is a methyl group, n is 0 to 14 and m=2 to 10. The compound above, or a pharmaceutically acceptable acid or salt thereof, can be used as an agent for inhibiting cancer cell growth when the compound is administered at a concentration in the range of 5 mg/L to 50 mg/L, with or without a pharmaceutically acceptable carrier.

A method of treating cancer in a mammal afflicted with cancer, comprising treating the afflicted mammal with a therapeutic amount of a phosphonate compound of the following general formula:

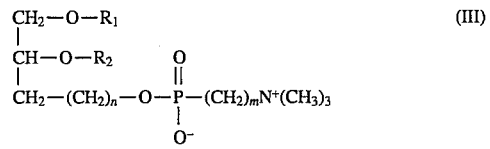

wherein R1 is an alkyl group containing 12 to 20 carbon atoms such as hexadecyl or octadecyl, R2 is a methyl group, n=0 or 1 and m=2 to 10. The compound above, or a phamaceutically acceptable acid or salt thereof, can be used as an agent for inhibiting cancer cell growth when the compound is administered at a concentration in the range of 5 mg/L to 50 mg/L, with or without a pharmaceutically acceptable carrier.

A method of treating cervical cancer, breast cancer, ovarian cancer or colorectal cancer in a mammal afflicted with cervical cancer, breast cancer, ovarian cancer or colorectal cancer, comprising treating the afflicted mammal with a therapeutic amount of a phosphonate compound of the following formula:

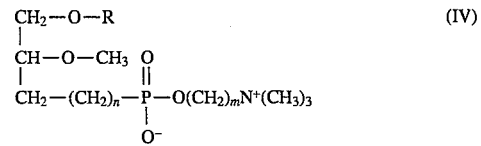

wherein R is an alkyl group containing 12 to 20 carbon atoms, specifically either hexadecyl or octadecyl; n=0 or 1 and m=2 to 4, The phosphonate compound above, or a pharmaceutically acceptable acid or salt thereof, is given orally, intramuscularly or intravenously, with or without a pharmaceutically acceptable carrier, in a concentration range of 5–50 mg/L.

A method for treating melanoma in a mammal afflicted with melanoma, comprising treating the afflicted mammal with a therapeutic amount of a phosphonate compound of the following formula:

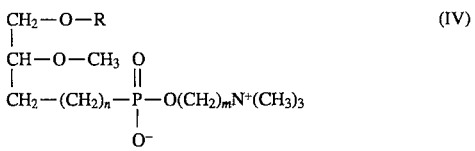 (IV)

wherein R is an alkyl group containing 12 to 20 carbon atoms, specifically either hexadecyl or octadecyl; n=0 or 1 and m=2 to 4. The phosphonate compound above, or a pharmaceutically acceptable acid or salt thereof, is applied topically, with or without a pharmaceutically acceptable carrier, in a concentration range of 5–100 mg/mL.

A method of treating cancer of colorectal, lung, melanoma, lymphoma or leukemia in a mammal in need of cancer treatment comprising administering to said mammal a therapeutically effective amount of a thioalkylphelsphonate of the following formula:

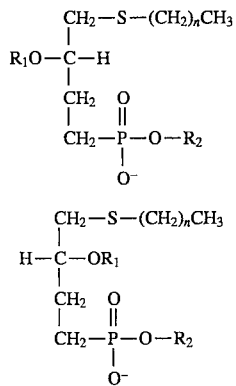

wherein n is 8 to 22; $R_1$ is $CH_3$, and $R_2$ is a choline and therapeutically effective pharmaceutically acceptable salts thereof.

The phosphonolipid is administered to the mammal at a dosage of 5 to 50 mg/l, either alone or in association with a pharmaceutically acceptable carrier or lipid vessicles of liposome.

A method of treating cancers of colorectal, melanoma or lungs in a mammal in need of cancer treatment comprising administering to said animal a therapeutically effective amount of a phosphonolipid of the following formula:

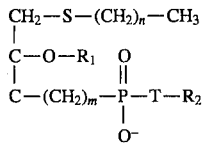

wherein n is 15; $R_1$ is an alkyl group of one to four carbon atoms; m is 0 to 2; T is an oxygen atom or methylene; and $R_2$ is choline, and therapeutically effective pharmaceutically acceptable salts thereof.

A method of treating cancer in a mammal in need of cancer treatment comprising administering to said mammal a therapeutically effective amount of 4-hexadecylthio-3-O-methyl butane-3-phosphonocholine with the methoxy group at the C2 position in R or S configuration, or pharmaceutically acceptable salts thereof. The phosphonolipid can be administered to the mammal at a dosage of 5 to 50 mg/l, either alone or in a pharmaceutically acceptable carrier such as lipid mixtures of liposome.

A thiophosphonolipid of the following formula:

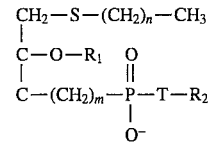

wherein n is 15 to 17; $R_1$ is $CH_3$; m is 0 to 2; T is an oxygen atom or a methylene; and $R_2$ is a choline and therapeutically effective pharmaceutically acceptable salts thereof.

A compound as described wherein n is 15 or 17; $R_1$ is $CH_3$; m is 0 to 2; T is an oxygen atom or a methylene; and $R_2$ is a choline and therapeutically effective pharmaceutically acceptable salts thereof for treatment of melanoma, colorectal, lymphoma, leukemia, or lung cancers.

A compound as described wherein n is 15 to 17; $R_1$ is an alkyl group of one to two carbon atoms; m is 0 to 2; T is an oxygen atom; and $R_2$ is choline, and therapeutically effective pharmaceutically acceptable salts or lipid carriers of any hydrocarbons used as carriers.

A compound as described wherein n is 15; $R_1$ is $CH_3$; m is 0 to 2; T is an oxygen atom; and $R_2$ is choline, and therapeutically effective pharmaceutically acceptable salts thereof applied orally, subcutaneously, intramuscularly, intravenously or topically for treatment of melanoma, lymphoma, leukemia, colorectal or lung cancers.

These phosphonates are useful as anti-cancer agents since they inhibit growth of malignant cells.

The phosphonate compounds as described above or claimed include either of the opposite stereochemical configurations (R) or (S), or a mixture thereof.

DETAILED DESCRIPTION OF SPECIFIC EMBODIMENTS OF THE INVENTION

1. Production of the Phospholipids of the Invention (a) Synthesis of Phosphonocholines Diethyl phosphite is treated with hexadecyl (or octadecyl) bromide in a Michaelis-Becker reaction, giving the corresponding diethyl ester. The alkyl phosphonic acid is formed in situ from the ester, then treated with 2.1 equivalents of pyridine at 0° C. in tetrahydrofuran, followed by 2.1 equivalents of oxaloyl chloride at −78° C. under nitrogen. The phosphonic acid dichloride thus obtained is treated with either (R)-2-0-benzylglycerol (for conversion to phosphonoglycerol) or with ethylene glycerol to give the phospholane intermediate, which is reacted with triethylamine in acetonitrile at 75° C. in a pressure bottle to give phosphonocholine. The intermediates and products are purified by chromatography on silica gel G or by high-pressure liquid chromatography. The structures are established by nuclear magnetic resonance spectroscopy, mass spectrometry, and by elemental analysis.

(b) Production of glycerol-linked phosphonolipids

The rac-phosphonic acid described above is prepared by proceeding according to the following sequence of reactions. First a ,n-alkyl allyl ether is reacted with methanol in the presence of zinc oxide and iodine; alkyl groups other than methyl can be conveniently introduced by this method (reference:

Rosenthal, A. F.; Kosolapoff, G. M.; Geyer, R. P. *Recl. Trav. Chim. Pays-Bas* 1964, 83, 1273). The 1-0-alkyl-2-0-methyliodopropane is treated with triethyl phosphite, affording the corresponding diethyl phosphonate ester, which is hydrolyzed to give the phosphonic acid. Phosphonocholine is obtained by reaction with dry choline tosylate (9 equivalents) in the presence of trichloroacctonitrile in pyridine at 50° C. for 2 days.

The corresponding glycerol-linked phosphonoethanolamine is prepared by reaction of the phosphonic acid with N-(tert-butoxycarbonyl)-ethanolamine (N-t-Boc-ethanolamine), in the presence of trichloroacetonitrile or 1H-tetrazole; after purification of the coupling product by silica gel chromatography, the Boc protecting group is removed under standard conditions (50% trifluoracetic acid in dichloromethane at 0° C.).

The corresponding glycerol-linked phosphonoserine is prepared in a similar fashion, using N-tritylserine methyl ester for coupling with the phosphonic acid. The acid-labile trityl group is removed by treatment with 0.1M hydrochloric acid in tetrahydrofuran-water (1:1), and then the methyl ester is hydrolyzed by using 0.2M sodium hydroxide. Purification is by silica gel chromatography.

2. Biological Activity

In vitro tests, such as the $^3$H-thymidine incorporation assay and the colonogenic cell survival assay, as well as in vivo techniques have been conducted to establish that phosphonates inhibit the growth of or kill cancer cells. The testing methodologies are described below.

Experiments were performed using a number of different tumor cell lines. Tumor cells were cultured in RPMI-1640 medium supplemented with 10% fetal bovine serum, penicillin (50 units/mL), streptomycin (50 μg/mL) and mercaptoethanol (5 μg/mL) in an atmosphere of 5% $CO_2$. The cells were passaged weekly by serial 1/10 to 1/10,000 dilutions. The cell viability and growth were constantly monitored by staining with trypan blue exclusion dye or the incorporation of tritiated thymidine.

Inhibition of $^3$H-thymidine incorporation into the DNA of cells by a test compound is an indirect measurement of cell kill or growth inhibition, and reflects the anti-cancer activity of the compound.

Tumor cells (2×10$^4$ cells/well) were placed in 200 μL of medium in 96-well plastic microtiter plates; a further 5 μL of medium either with or without phosphonate was added. After incubation for 24, 48 or 72 hours at 37° C. in a humidified atmosphere containing 5% $CO_2$, the wells were pulsed with 0.1 μCi of $^3$H-thymidine for an additional 24 hours. The cells were then harvested using a Brandel cell harvester (model M-12) and collected on Whatman glass microfilters. The radioactivity associated with the filters was quantified in a liquid scintillation counter, and the amount of $^3$H-thymidine incorporated into tumor cells treated with the phosphonate compound was calculated as a percentage of the amount of $^3$H-thymidine incorporated into untreated tumor cells.

Inhibition of colony formation in soft agar medium (colonogenic cell survival assay) is a more rigorous and direct measurement of cell kill or growth inhibition, and reflects the anti-cancer activity of the test compound. Briefly, tumor cells were cultured in petri dishes in methylcellulose, with or without a phosphonate test compound, and the number of colonies formed during a 5-day incubation period were counted.

EXAMPLE 1

Activity of phosphonates against leukemia and lymphoma

It has been discovered that a phosphonate compound of the following formula:

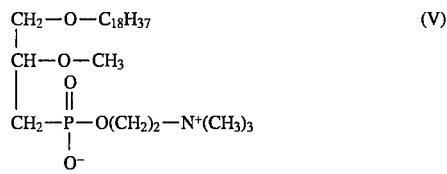

inhibits thymidine incorporation into DNA of two leukemic cell lines: (1) WEHI-3B, a mouse myelomonocytic leukemic cell line: and (2) HL-60, a human myeloleukemic cell line. This effect is indicative of the anti-cancer activity of the above phosphonate (compound V).

Table I shows the effect of 24 hours' exposure to various concentrations of the phosphonate compound of the above formula (compound V) on the incorporation of $^3$H-thymidine into DNA (described above) by WEHI-3B tumor cells.

TABLE 1

$^3$H-thymidine incorporation by WEHI-3B tumor cells exposed to various concentrations of phosphonate (compound V) for 24 hours.

| Phosphonate concentration (μM) | Thymidine uptake (% of control) mean ± s.d. |
|---|---|
| 0 | 100 |
| 0.62 | 137 ± 6 |
| 1.25 | 93 ± 7 |
| 2.5 | 91 ± 4 |
| 5 | 88 ± 11 |
| 10 | 76 ± 6 |
| 20 | 48 ± 4 |
| 40 | 43 ± 15 |

Table 2 shows the effect of 48 hours of exposure to various concentrations of the phosphonate compound of the above formula (compound V) on the incorporation of $^3$H-thymidine into DNA (described above) by WEHI-3B and HL-60 rumor cells.

TABLE 2

$^3$H-thymidine incorporation by WEHI-3B and HL-60 tumor cells exposed to various concentrations of phosphonate (compound V) for 48 hours.

| Phosphonate concentration (μM) | Thymidine uptake (% of control) mean ± s.d., n = 8 | |
|---|---|---|
| | WEHI-3B cells | HL-60 cells |
| 0 | 100 | 100 |
| 0.62 | 93 ± 6 | 84 ± 5 |
| 1.25 | 90 ± 5 | 76 ± 4 |
| 2.5 | 86 ± 8 | 63 ± 4 |
| 5 | 61 ± 6 | 24 ± 3 |
| 10 | 23 ± 2 | 3 ± 2 |
| 20 | 18 ± 8 | 1 ± 0 |

Table 3 shows the effect of 72 hours of exposure to various concentrations of the phosphonate compound of the above formula (compound V) on the incorporation of $^3$H-thymidine into DNA (described above) by WEHI-3B and HL-60 tumor cells.

TABLE 3

$^3$H-thymidine incorporation by WEHI-3B and
HL-60 tumor cells exposed to various concentrations of
phosphonate (compound V) for 48 hours.

| Phosphonate concentration (μM) | Thymidine uptake (% of control) mean ± s.d., n = 8 | |
|---|---|---|
| | WEHI-3B cells | HL-60 cells |
| 0 | 100 | 100 |
| 0.62 | 85 ± 3 | 93 ± 4 |
| 1.25 | 86 ± 4 | 81 ± 4 |
| 2.5 | 82 ± 6 | 66 ± 3 |
| 5 | 60 ± 4 | 16 ± 4 |
| 10 | 26 ± 3 | 5 ± 1 |
| 20 | 10 ± 3 | 1 ± 0.9 |

As can be seen from Tables 1, 2 and 3, a phosphonate compound of the formula shown above (compound V) inhibits the $^3$H-thymidine incorporation into DNA of both mouse-derived (WEHI-3B) and human-derived (HL-60) leukemic cell lines over 24, 48 and 72 hours' exposure. This effect is dose-dependent, and demonstrates the anti-cancer activity of phosphonates.

It has been discovered that a phosphonate compound of the following formula:

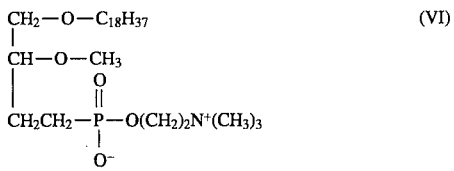
(VI)

also inhibits thymidine incorporation into DNA of several cancer cell lines. This effect is indicative of the anti-cancer activity of the above phosphonate (compound VI).

Table 4 shows the effect of various concentrations of the phosphonate compound of the above formula (compound VI) on the incorporation of $^3$H-thymidine into DNA (described above) by WEHI-3B tumor cells after 1.2 and three days' exposure to the compound.

TABLE 4

$^3$H-thymidine incorporation by WEHI-3B tumor cells
exposed to various concentrations of phosphonate
(compound VI) for 1, 2, or 3 days.

| Phosphonate concentration (μM) | Thymidine uptake (% of control) Mean, n = 5 | | |
|---|---|---|---|
| | Day 1 | Day 2 | Day 3 |
| 0 | 100 | 100 | 100 |
| 1.25 | 95 | 84 | 77 |
| 2.5 | 72 | 67 | 54 |
| 5 | 34 | 22 | 12 |
| 10 | 18 | 13 | 10 |
| 20 | 8 | 2 | 1 |
| 40 | 3 | 2 | 2 |

As can be seen from Table 4, a phosphonate compound of the formula shown above (compound VI) inhibits the $^3$H-thymidine incorporation into DNA of a mouse-derived (WEHI-3B) leukemic cell line over 1, 2 and 3 days' exposure. This effect is dose-dependent, and demonstrates the anti-cancer activity of phosphonates.

Phosphonates were shown to be highly effective in preventing the growth of a number of mouse-derived cancer cell lines, L1210, a mouse lymphoma cell line which is derived from lymph nodes in mice; P388, a macrophage lineage which, when grown under the skin, produces a rumor; and WEHI-3B, a myelomonocytic lineage that grows as a solid rumor and metastasizes to the lungs, blood, spleen and various other organs, were evaluated for their sensitivity to the cytotoxic activity of phosphonates using the colonogenic cell survival assay (described above).

Table 5 shows the effect of the phosphonate compound of the following formula on the formation of colonies by the three tumor cell lines described above.

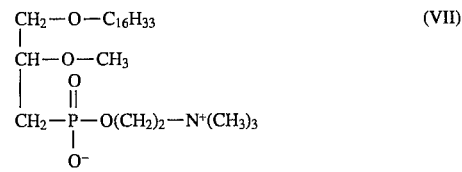
(VII)

TABLE 5

Colony formation by P388, L1210 and WEHI-3B
tumor cells exposed to various concentrations of
phosphonate (compound VII).

| Phosphonate concentration (μM) | Colonies formed after 5 days (% of control) Mean, n = 5 | | |
|---|---|---|---|
| | P388 | L1210 | WEHI-3B |
| 0 | 100 | 100 | 100 |
| 1.25 | 88 ± 6 | 91 ± 7 | 88 + 6 |
| 2.5 | 79 ± 8 | 80 ± 11 | 60 + 6 |
| 5 | 61 ± 7 | 55 ± 4 | 48 + 5 |
| 10 | 56 ± 7 | 42 ± 5 | 34 + 4 |
| 20 | 29 ± 4 | 22 ± 3 | 13 + 3 |
| 40 | 16 ± 2 | 14 ± 5 | 2 + 1 |

As can be seen from Table 5, phosphonate compounds of the formula shown above (compound VII) inhibit colony formation in cultures of leukemic and lymphomic cell lines when exposed for five days to the phosphonate compound. This effect is dose-dependent, and demonstrates the anti-cancer activity of phosphonates.

The anti-cancer activity of the phosphonate of the following formula:

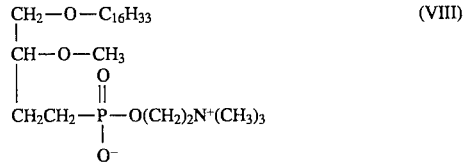
(VIII)

against human leukemia and lymphoma was also studied using the colonogenic cell survival assay. DHL4, a human B cell lymphoma; HeL, a human erythroid leukemia: JRT3T3, a human T-cell lymphoma; and KG 1α, a human mycloid leukemia, were evaluated for their sensitivity to the cytotoxic activity of the phosphonate of the above formula (compound VIII).

Table 6 shows the anti-cancer activity of the above phosphonate (compound VIII) on these four tumor cell lines.

TABLE 6

Colony formation by DHL4, HeL, JRT3T3 and KG1a tumor
cell lines exposed to various concentrations of
phosphonate (compound VIII).

| Phosphonate concentration (μM) | Colonies formed after 5-days (% of control) Mean ± S.D., n = 5 | | | |
|---|---|---|---|---|
| | DHL4 | HeL | JRT3T3 | KG1α |
| 0 | 100 | 100 | 100 | 100 |

TABLE 6-continued

Colony formation by DHL4, HeL, JRT3T3 and KG1a tumor cell lines exposed to various concentrations of phosphonate (compound VIII).

| Phosphonate concentration | Colonies formed after 5-days (% of control) Mean ± S.D., n = 5 | | | |
|---|---|---|---|---|
| (µM) | DHL4 | HeL | JRT3T3 | KG1α |
| 1.25 | 76 ± 7 | 91 ± 8 | 87 ± 6 | 78 ± 8 |
| 2.5 | 61 ± 5 | 72 ± 5 | 65 ± 7 | 56 ± 6 |
| 5 | 42 ± 6 | 58 ± 4 | 34 ± 5 | 41 ± 4 |
| 10 | 18 ± 4 | 26 ± 5 | 20 ± 3 | 15 ± 3 |
| 20 | 5 ± 1 | 12 ± 3 | 8 ± 2 | 7 ± 1 |
| 40 | 0 | 1 ± 0.5 | 3 ± 1 | 4 ± 1 |

As can be seen from Table 6, phosphonate compounds of the formula shown above (compound VIII) inhibit colony formation in cultures of human leukemic and lymphomic cell lines when exposed for five days to the phosphonate compound. This effect is dose-dependent, and demonstrates the anti-cancer activity of phosphonates.

Phosphonates were shown to be highly effective in vivo in retarding tumor growth in mice. WEHI-3B (mouse myelomonocytic leukemia) rumor cells, which showed sensitivity to the cytotoxic activity of phosphonates in both the $^3$H-thymidine uptake assay and the colonogenic cell survival assay, were grown under the skin in BALB/C mice at 1×10$^6$ cells per mouse. After 3 days one group (n=5) of mice received 500 µg (approximately 25 mg/Kg body weight) of the phosphonate compound of the following formula daily by intramuscular (IM) injection. The size of the resulting tumor was measured using a caliper:

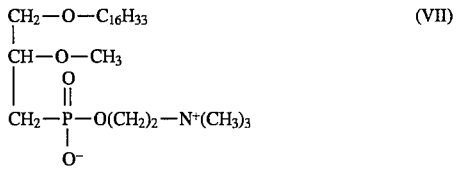 (VII)

Table 7 shows the tumor size in untreated and phosphonate-treated (compound VII) and mice.

TABLE 7

WEHI-3B tumor gowth in untreated and phosphonate-treated (compound VII) Balb/C mice.

| Days after implantation | Tumor volume in cm$^3$ Mean ± s.d., n = 5 | |
|---|---|---|
| | Untreated mice | Phosphonate-treated mice |
| 3 | 0.009 ± 0.001 | 0.000 ± 0.000 |
| 15 | 0.024 ± 0.004 | 0.000 ± 0.000 |
| 17 | 0.138 ± 0.062 | 0.000 ± 0.000 |
| 20 | 0.219 ± 0.089 | 0.036 ± 0.010 |
| 22 | 0.705 ± 0.234 | 0.117 ± 0.017 |
| 24 | 0.952 ± 0.111 | 0.172 ± 0.025 |

As can be seen from Table 7, phosphonates are potent anti-cancer agents effective in vivo: treatment of mice with 25 mg/Kg body weight per day of phosphonate (compound VII), given intramuscularly, delayed the onset of tumor growth and reduced the tumor growth significantly.

The effects of phosphonates in a mouse model of lymphoma were also studied. Mice (CD 1) were injected with 1×10$^6$ L1210 (B-cell lymphoma) cells intraperitoneally. In one group the mice received the phosphonate compound of the following formula at 10 mg/kg per day intramuscularly, while a second group of mice received no treatment:

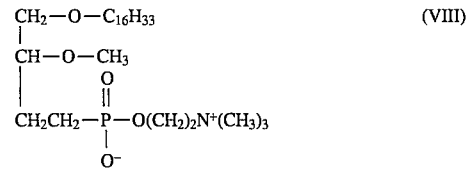 (VIII)

Table 8 shows the percentage of untreated and phosphonate-treated (compound VIII) mice which survived after the injection of L1210 mouse lymphoma cells.

TABLE 8

% Survival of untreated and phosphonate-treated (compound VIII) CD1 mice injected with L1210 mouse lymphoma cells.

| Days after injection of L1210 lymphoma cells | % Survival | |
|---|---|---|
| | Untreated CD1 mice | Phosphonate-treated CD1 mice |
| 0 | 100 | 100 |
| 7 | 83 | 100 |
| 8 | 50 | 100 |
| 19 | 33 | 100 |
| 21 | 0 | 100 |

As can be seen from Table 8, the results clearly demonstrated that phosphonates were highly effective in mitigating death due to lymphoma. The untreated mice started to die 7 days after cancer cell injection as the lymph nodes and marrow grew extensive numbers of cancer cells. None of the phosphonate-treated (compound VIII) animals died up to 21 days of observation.

The studies shown above clearly demonstrate the anti-cancer activity of phosphonates against leukemia and lymphoma.

EXAMPLE 2

Activity of phonates against lung cancer

Lewis Lung carcinoma (LLC), a cancer cell linc derived from lung minors of mice, was evaluated for its sensitivity to the cytotoxic activity of phosphonates of the following structure using the colonogenic cell survival assay (described above):

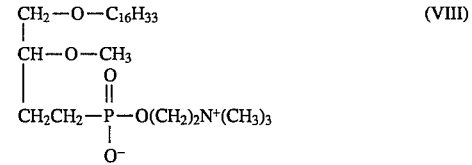 (VIII)

Table 11 shows the anti-cancer activity of phosphonates of the above formula (compound VIII) on the LLC lung cancer cell line.

TABLE 11

Colony formation by LLC tumor cells exposed to various concentrations of phosphonate (compound VIII).

| Phosphonate concentration (µM) | Colonies formed after 5 days (% of control) Mean, n = 5 |
|---|---|
| 0 | 100 |
| 1.25 | 97 ± 9 |
| 2.5 | 81 ± 6 |
| 5 | 67 ± 5 |

TABLE 11-continued

Colony formation by LLC tumor cells exposed to
various concentrations of phosphonate (compound VIII).

| Phosphonate concentration (μM) | Colonies formed after 5 days (% of control) Mean, n = 5 |
|---|---|
| 10 | 53 ± 4 |
| 20 | 37 ± 5 |
| 40 | 19 ± 6 |

As can be seen in Table 11, phosphonates of the formula shown above (compound VIII) inhibit colony formation by LLC lung cancer cells. This effect is dose-dependent, and demonstrates the anti-cancer activity of phosphonates against lung cancer.

The effects of the phosphonate compound of the following formula on LLC tumor growth in mice was examined:

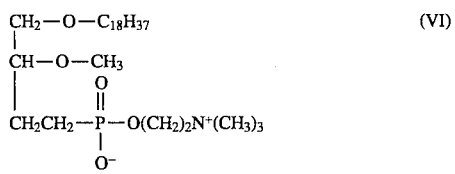

BALB/C mice were injected with 3-Lewis lung carcinoma cells under the skin at the back. Three days after injection of the tumor cells, treatment with the phosphonate shown above (compound VI) (50 mg/day orally once a day) was initiated in one group of mice, while a second group of mice received only the carrier, mucilage of tragacanth.

Table 12 shows the tumor size in untreated and phosphonate-treated (compound VI) mice.

TABLE 12

LLC tumor growth in untreated and phosphonate-treated
(compound VI) BALB/C mice

| Days after tumor injection | Tumor volume (mm³) | |
|---|---|---|
| | untreated mice | phosphonate-treated mice |
| 0 | 0 | 0 |
| 7 | 30 | 0 |
| 10 | 120 | 0 |
| 17 | 250 | 100 |
| 18 | 432 | 175 |
| 20 | 670 | 252 |
| 22 | 810 | 500 |

As seen from Table 12, the first sign of a detectable tumor was observed in untreated animals seven days after the cell injection. In the phosphonate-treated (compound VI) animals, the minor growth was retarded by approximately 6 days. The tumor size in the phosphonate-treated (compound VI) animals remained below that in the untreated animals throughout the experiments. The studies shown above demonstrate the anti-cancer activity of phosphonates against lung cancer.

EXAMPLE 3

Activity of phosphonates against cervical
carcinoma and breast adenocarcinoma

It has been discovered that a phosphonate compound of the following structure:

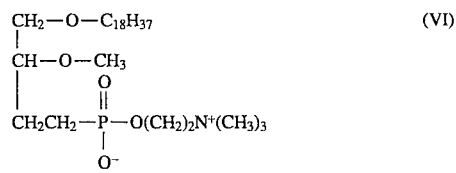

inhibits thymidine incorporation into DNA of a human cervical carcinoma (C-41) cell line. This effect is indicative of the anti-cancer activity of the above compound.

Table 9 shows the effect of various concentrations of the phosphonate compound of the above formula (compound VI) on the incorporation of 3H-thymidine into DNA (described above) by C-41 tumor cells.

TABLE 9

$^3$H-thymidine incorporation by C-41 tumor cells exposed to
various concentrations of phosphonate (compound VI).

| Phosphonate concentration (μM) | Thymidine uptake (% of control) Mean, n = 3 |
|---|---|
| 0 | 100 |
| 2.5 | 88 |
| 5 | 63 |
| 10 | 42 |
| 20 | 41 |
| 40 | 16 |

As can be seen from Table 9, a phosphonate compound of the formula shown above (compound VI) inhibits the $^3$H-thymidine incorporation into DNA of C-41 cervical carcinoma cells. This effect is dose dependent, and demonstrates the anti-cancer activity of phosphonates against cervical carcinoma.

The effects of the phosphonate compound of the following formula on human tumors were examined in the colonogenic cell survival assay (described above) using two human solid tumor cell lines. The C-41 cell line, derived from human cervical carcinoma, and the MCF-7 cell line, derived from human breast adenocarcinoma, were evaluated for their sensitivity to the cytotoxic action of phosphonates:

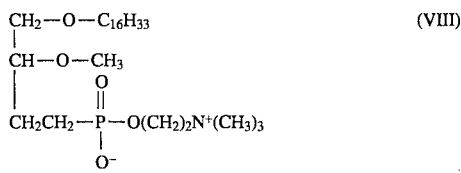

Table 10 shows the anti-cancer activity of the phosphonate of the formula shown above (compound VIII) on human cervical and breast tumor cell lines.

TABLE 10

Colony formation by C-41 and MCF-7 tumor cells exposed to various concentrations of phosphonate (compound VII).

| Phosphonate concentration (μM) | Number of colonies after 5 days (% of control) mean ± s.d., n = 5 | |
| --- | --- | --- |
| | C-41 | MCF-7 |
| 0 | 100 | 100 |
| 1.25 | 97 ± 8 | 102 ± 10 |
| 2.5 | 87 ± 7 | 89 ± 11 |
| 5 | 71 ± 8 | 84 ± 6 |
| 10 | 52 ± 6 | 68 ± 5 |
| 20 | 31 ± 4 | 47 ± 6 |
| 40 | 12 ± 2 | 16 ± 3 |

As can be seen from Table 10, phosphonate compounds of the formula shown above (compound VIII) inhibit colony formation by both cervical (C-41) and breast (MCF-7) cancer cells. This effect is dose dependent, and demonstrates the anti-cancer activity of phosphonates against cervical carcinoma and breast adenocarcinoma.

The studies shown above clearly demonstrate the anti-cancer activity of phosphonates against cervical carcinoma and breast adenocarcinoma.

EXAMPLE 4

Activity of phosphonates against human melanoma and colorectal cancer

The phosphonate compound of the following formula was tested against human melanoma and colorectal cancers:

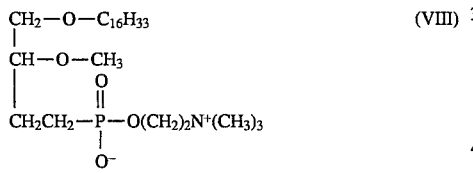

(VIII)

The anti-cancer activity of the phosphonate compound of the formula shown above (compound VIII) was examined in human melanoma and colorectal tumor cell lines using the colonogenic cell survival assay (described above). RPMI-7951 (human melanoma) and HT-29 (human colorectal cancer) tumor cell lines were evaluated for their sensitivity to the cytotoxic activity of the above phosphonate (compound VIII).

Table 13 shows the cytotoxic effect of the phosphonate compound of the formula shown above (compound VIII) against human melanoma (RPMI-7951) and colorectal (HT-29) cancers.

TABLE 13

Colony formation (% of control) of HT-29 and RPMI-7951 tumor cell lines exposed to various concentrations of phosphonate (compound VIII).

| Phosphonate concentration (μM) | Colonies formed (% of control) | |
| --- | --- | --- |
| | HT-29 | RPMI-7951 |
| 0 | 100 | 100 |
| 2.5 | 74 | 68 |
| 5 | 51 | 43 |
| 10 | 22 | 13 |
| 20 | 8 | 3 |
| 40 | 0 | 0 |

As can be seen in Table 13, phosphonates of the formula shown above (compound VII) inhibit colony formation by human melanoma (RPMI-7951) and colorectal (HT-29) cancer cell lines. This effect is dose-dependent, and demonstrates the anti-cancer activity of phosphonates against melanoma and colorectal cancer.

Studies were also performed with nude mice injected with the human colorectal cell line (HT-29) subcutaneously. The results of this study showed that the phosphonate compound of the formula shown above (compound VIII), given orally once a day at a dose of 5 mg/Kg body weight, retarded the tumor growth by 30–40%.

Similar studies were also performed with a human melanoma cell line (RPMI-7951) grown in nude mice. Mice injected with RPMI-7951 cell line intradermally developed tumors. When the mice were treated topically, twice a day, with an emulsion of 80 mg/mL of the phosphonate compound of the formula shown above (compound VIII), the growth and metastasis of tumors were retarded by approximately 60%. These results demonstrate that the phosphonate compound of the formula shown above (compound VIII) is useful as an anti-melanoma agent when applied topically.

It has been discovered that a phosphonate compound of the formula shown above (compound VIII) is also able to suppress metastasis of melanoma tumor cells implanted into the lungs of test animals via intravenous injection.

Highly metastatic B-16/F10 melanoma cells were injected into the tail veins of female C57BL/6 mice ($1\times10^5$ cells per mouse). Treatment of one group of mice with the phosphonate compound of the above formula (compound VIII), dissolved into 0.5mL ethanol, 0.5 mL cremaphor and 9.0 mL phosphate buffered saline, began three days after the tumor cells were injected. Intramuscular injections of 0.2 mL of the phosphonate emulsion (10 mg/kg/day) were given for 5 days per week for 2 weeks. A second group of mice were treated with Adriamycin (10 mg/kg given intravenously on days 0, 4 and 8) as a known anti-cancer drug control group, while a third group of mice received the vehicle emulsion alone. The mice were examined every day for general health, behaviour and body weight. Counts of metastatic melanomic tumor colonies found in the lungs, general observations of metastasis to distant organs and examination of organs (liver, kidneys, lungs and spleen) were taken at autopsy 4 weeks after treatment.

Table 14 shows the body weight and counts of metastatic melanomic tumor colonies found in the lungs for untreated mice and mice treated with Adriamycin or the phosphonate/compound of the formula shown above (compound VIII).

TABLE 14

Body weights (in grams) at days 0, 12 and 26 and counts of metastatic melanomic tumor colonies found in the lungs at autopsy.

| Day | Weight Mouse 1 | Weight Mouse 2 | Weight Mouse 3 | Weight Mouse 4 | Weight Mouse 5 | Weight Mouse 6 |
|---|---|---|---|---|---|---|
| Group 1 Vehicle only IM | | | | | | |
| 0 | 19 | 18 | 19 | 18 | 18 | 19 |
| 12 | 21 | 19 | 20 | 20 | 20 | 21 |
| 26 | 23 | 25 | 21 | 22 | 22 | 23 |
| Melanomic tumor colonies | 5 | 30 | 2 | 2 | 5 | 6 |
| Group 2 Adriamycin treated - 10 mg/kg IV (day 0, 4 and 8) | | | | | | |
| 0 | 20 | 19 | 18 | 18 | 19 | 21 |
| 12 | 18 | 17 | 15 | 17 | 17 | 21 |
| 26 | 22 | 20 | 19 | 19 | 21 | 22 |
| Melanomic tumor colonies | 0 | 0 | 0 | 0 | 0 | 0 |
| Group 3 Phosphonate-treated (compound VIII) - 10 mg/kg IM (5 days/week for 2 weeks) | | | | | | |
| 0 | 19 | 19 | 19 | 20 | 19 | 20 |
| 12 | 20 | 20 | 21 | 21 | 21 | 21 |
| 26 | 23 | 22 | 24 | 25 | 24 | 24 |
| Melanomic tumor colonies | 2 | 0 | 1 | 0 | 0 | 3 |

As can be seen from Table 14, phosphonate compounds of the above formula (compound VIII) are not toxic when administered intramuscularly at a dose of 10 mg/kg for 2 weeks, as shown by the weight of the mice and observations of animal behaviour and appearance. Treatment with the phosphonate compounds of the above formula (compound VIII) resulted in suppression of metastasis 26 days after the initiation of treatment. Upon autopsy of the above animals, no traces of melanomic metastasis to distant organs were evident in five of six animals, although melanomic tumor colonies were observed in the lungs. By comparison, all of the vehicle control mice had melanomic tumor colonies in their lungs as well as distant melanomic metastasis, while none of the Adriamycin-treated mice developed melanomic tumor colonies in their lungs. This study demonstrates that phosphonates are effective in inhibiting metastasis of melanomic tumors colonized in the lungs.

The studies shown above demonstrate the anti-cancer activity of phosphonates against human melanoma and colorectal cancer.

EXAMPLE 5

Cytotoxicity Data

A combination of $^3$H-Thymidine incorporation assay, colonogenic cell survival assay and MTT assay was used to determine cytotoxicity data of phosphonates in several mouse and human tumor cell lines. The concentration of phosphonate (compound VIII) which inhibits 50% of tumor cell growth ($IC_{50}$) is presented in Table 15.

TABLE 15

Cytotoxicity of phosphonate (compound VIII) in various mouse and human cancer cell lines, expressed as the concentration which inhibits 50% of tumor cell growth ($IC_{50}$) in $^3$H-thymidine uptake, colonogenic cell survival and MTT assays.

| Cell line | $IC_{50}(\mu M)$ |
|---|---|
| WEHI-3B (mouse granulocytic leukemia) | 2.5 |
| LLC (mouse Lewis lung carcinoma) | 10.6 |
| P388 (mouse monocytic leukemia) | 4.5 |
| P388 DR (drug resistant P388) | 5.0 |
| L1210 (mouse B-cell lymphoma) | 5.0 |
| RPMI (advanced human melanoma) | 9 |
| HT29 (human colon cancer) | 9 |
| HCT-116 (human rectal cancer) | 12 |
| MCF-7 (human breast cancer) | 35.3 |
| 2008 (human ovarian cancer) | 27.8 |
| MeWo (human melanoma cancer) | 15.7 |

As can be seen from Table 15, phosphonates are effective against leukemia, lymphoma, lung, colorectal, breast, ovarian and melanoma cancers.

From the studies presented in Examples 1, 2, 3, 4, and 5, it may be concluded that phosphonates are effective anti-cancer drugs that can suppress metastasis and reduce morbidity and mortality caused by leukemia, lymphoma, cervical carcinoma, breast adenocarcinoma, ovarian cancer, lung cancer, colorectal cancer and melanoma.

Synthesis of Long-Chain 4-Alkylthio-3-methoxy-3-(R or S)-methoxybutane phosphonocholine Synthesis of the following formula is carded out as below:

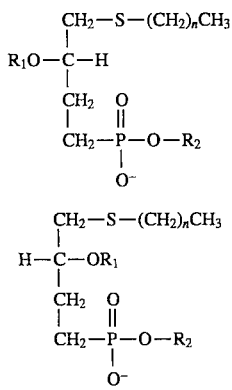

wherein n is 8 to 22; $R_1$ is an alkyl group, and $R_2$ is a choline or, inositol head group.

Thioethers having a phosphonocholine moiety, and a methoxy group at $C_2$, with the S or R configuration, were prepared as follows. 1-Thioalkyl-sn-glycerol in which the thioalkyl group contains between 8 to 22 carbon atoms was subjected to a Mitsunobu reaction with triphenylphosphine and diethyl azodicarboxylate, thereby forming thioalkyl (S)-2 oxiranemethyl thioether. The epoxide ring of the latter compound was opened in a regiospecific and stereospecific manner with dimethyl methanephosphonate and n-butyl-lithium in the presence of boron trifluoride etherate in tetrahydrofuran at −78° C. The resulting dimethyl 4-(alkylthio)-3(R or S)-hydroxybutlphosphonate was methylated using diazomethane in dryethyl ether in the presence of silica gel at 0° C. The methyl ester groups were hydrolyzed with trimethylsilyl bromide followed by aqueous workup, yielding the phosphonic acid as a white solid. The choline group was coupled as a head group to the phosphonic acid to complete the preparation of the compound. The product was purified by silica gel column chromatography, eluting with choloroform-methanol-water(65:25:4). The enantiomer, 4-(alkylthio)-3-(R)-methoxybutane phosphonate, was prepared from 3-thioalkyl-sn-glycerol by the same procedures.

EXAMPLE

Anti-Neoplastic Activity of Thiophosphonolipids

The biological activities of 4-hexadecylthio-3(S)-3-methoxybutane-1-phosponocholine and its enantiomer 4-hexadecylthio-3(R)-3-methoxybutane-1-phosphonocholine were studied on several cancer cell lines. Table 16 shows the cytotoxic activity of each compound on a myelomonocytic leukemic cell line (WEHI-3B). The cell viability, was determined as percent[$^3$H]thymidine uptake into the cell DNA. The following results are mean of five samples ± S.D.

TABLE 16

| Drug Concentration | Cell Viability (% of Control) | |
| --- | --- | --- |
| (µM) | S-isomer | R-isomer |
| 0 | 100 ± 0.7 | 100 ± 0.6 |
| 6.25 | 55 ± 0.5 | 61 ± 0.4 |
| 12.50 | 31 ± 3.4 | 24 ± 2.7 |
| 25 | 21 ± 0.2 | 22 ± 4.6 |
| 50 | 2 ± 1.4 | 12 ± 1.2 |

Table 17 tabulates data obtained with two differrent phosphonate analogs using a colonogenic assay. Colonogenic assay is one of the most trusted tests for determination of effectiveness of an anti-cancer agent. The test is based on the formation of tumor colonies in vitro in a methyl cellulose or soft agar medium. The following results were obtained with the formation of colonies in methyl cellulose medium after five days in the presence or absence of four phosphonate analogs, two with a thioalkyl chain and two with an alkyloxy chain.

TABLE 17

| Drug Concentration | WEHI-3B Colonies Formed (Percentage of Control) | |
| --- | --- | --- |
| Concentration (µM) | Compound 1 | Compound 2 |
| 0 | 100 | 100 |
| 0.6 | 88 | 54 |
| 1.25 | 95 | 44 |
| 2.5 | 55 | 36 |
| 5 | 52 | 21 |
| 10 | 22 | 5 |
| 20 | 9 | 0 |

Compound 1 = 4-hexadecylthio-3-O-methyl-3(S)-butane-phosphonocholine
Compound 2 = 4-hexadecylthio-3-O-methyl-3(R)-butane-phosphonocholine The efficacy of 4-hexadecylthio-3-methoxybutane phosphonocholine on the growth of a mouse granuloma tumor was evaluated. The P388 cell line was cultured in a soft agar in the presence and absence of various concentrations of thioalkylphosphonate for 5 days, the number of tumor colonies formed during this period of time was registered. As seen from Table 18, the drug significantly reduced the number of tumor cells in this preparation.

TABLE 18

| S-Thioalkylphosphonocholine (µM) | Number of colonies Formed (% of Control) |
| --- | --- |
| 0.62 | 55 |
| 1.25 | 43.7 |
| 2.5 | 41 |
| 5 | 29 |
| 10 | 3 |
| 20 | 1 |

The effectiveness of S-thioalkylphosphonate on the growth of a lymphoma cell line was also investigated. L1210 is a mouse B-Cell tumor (lymphoma), was tested in soft agar for susceptibility to the cytotoxic action of thioalkylphosphonate. As shown in table 19, the drug also killed the pymphoma cell type effectively.

TABLE 19

| S-Thioalkylphosphophonocholine (µM) | Number of Colonies Formed (% of Control) |
| --- | --- |
| 0.65 | 65 |
| 1.25 | 47 |
| 2.5 | 30.5 |
| 5 | 30 |
| 10 | 20.5 |
| 20 | 14 |

We also provide data on the activity of S-thioalkylphosphonate to delay growth of tumor in the mice. WEHI-3B cells were grown in mice under the skin. Three days after the injection of cancer cells the mice received daily 10 mg/kg thialkylphosphonate for 21 days. The control mice received the saline alone instead of the drug. After 21 days, the tumor volume was measured. As shown in Table 20, the drug reduced tumor size by about 50%. The tumor volume was measured in $CM^3$.

TABLE 20

| Tumor Volume at Day 21 | |
| --- | --- |
| Control | Drug Treated |
| 0.642 ± 0.128 | .0359 ± 0.128 units cm$^3$ |

Table 21 shows the effect of S-thioalkylphosphonate on human colon carcinoma (HT29) and on human melaoma (RPM1795 1) cell lines.

TABLE 21

| S-thioalkylphosphonate cells µM | HT29 cells | RPMI7915 (% of control) |
| --- | --- | --- |
| 0 | 100 | 100 |
| 0.6 | 99 | 98 |
| 1.25 | 83 | 80 |
| 2.5 | 71 | 78 |
| 5 | 54 | 63 |
| 10 | 45 | 40 |
| 20 | 18 | 29 |
| 40 | 1 | 0 |

The results demonstrated the thioalkylphosphonates are active against human colorectal and skin melonoma.

USAGE AND DOSAGE

The compounds of the invention are useful as anti-cancer agents, and may be administered safely by either parenteral, oral or topical routes in pharmaceutical preparations such as injections, tablets, capsules, liquid preparations or ointments. These preparations are used by an appropriate route of administration, depending on the specific affliction, patient conditions and other factors. Injections may be given intravenously, intramuscularly, intradermaily or subcutanously. The dose of compound can be selected based on the patient weight, treatment regimen or purpose of administration, generally within the range of 5 to 50 mg/Kg. These compound preparations may be administered 1 to 4 times daily, daily, at 2 to 7 day intervals, or as otherwise necessary to maintain a therapeutic level of the compound in body tissues, depending on the specific affliction, patient conditions, treatment regimen or purpose of administration.

Injections, intravenous infusions and similar preparations are prepared by conventional methods in either aqueous solution or physiological saline containing 20% propylene glycol and a preservative such as 0.5% ascorbic acid, with an upwardly adjusted pH in phosphate buffer. The drug solution is sterilized by passing it through a 22 μm filter, and distributed into glass vials in approximately 1 mL aliquots to provide a unit dosage. The aliquots are then lyophilized, and the vials tightly stoppered and capped to maintain sterility. The drug may be reconstituted in the vial by the addition of physiological saline or aqueous diluent.

Tablets are prepared by conventional methods. Unit dosage tablets can be prepared by compressing a mixture of 40 mg of phosphonate, 200 mg of lactose, and 50 mg Avicel™ into the form of a tablet. A similar drug mixture may also be contained in unit dose within a cellulose-based capsule.

An ointment or cream may also be prepared by conventional methods by mixing the phosphonate compound in a commercially-available glycerine-based cream. The cream is applied topically directly to the afflicted area.

The compounds of the invention may also be administered in the form of a liposome. A mixture of phosphonate and lecithin is mechanically treated to form a bilayer (one side hydrophilic, the other hydrophobic) which spontaneously forms micelles (liposomes). These may be filtered to obtain liposomes of uniform size (approximately 10 nm) and dose (approximately 50 mg/L). Liposomes are administered as an intravenous solution.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of treating colorectal cancer in a mammal afflicted with colorectal cancer, comprising treating the afflicted mammal with a therapeutic amount of a phosphonate compound of the formula:

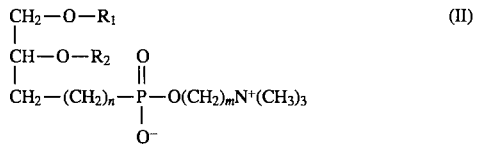

wherein $R_1$ is an alkyl group containing 12 to 20 carbon atoms, $R_2$ is a methyl group, n=0 to 14 and m=2 to 10, or enantiomer thereof, or a mixture of stereoisomers.

2. A method of treating melanoma in a mammal afflicted with melanoma, comprising treating the afflicted mammal with a therapeutic amount of a phosphonate compound of the formula:

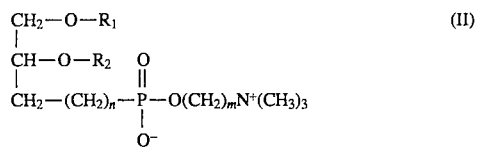

wherein $R_1$ is an alkyl group containing 12 to 20 carbon atoms, $R_2$ is a methyl group, n=0 to 14 and m=2 to 10, or enantiomer thereof, or a mixture of stereoisomers.

3. A method of treating cervical cancer in a mammal afflicted with cervical cancer, comprising treating the afflicted mammal with a therapeutic amount of a phosphonate compound of the formula:

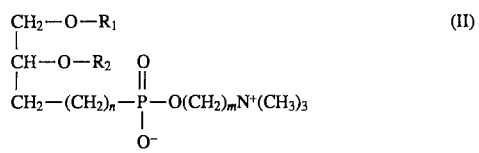

wherein $R_1$ is an alkyl group containing 12 to 20 carbon atoms, $R_2$ is a methyl group, n=0 to 14 and m=2 to 10, or enantiomer thereof, or a mixture of stereoisomers.

4. A method of treating breast cancer in a mammal afflicted with breast cancer, comprising treating the afflicted mammal with a therapeutic amount of a phosphonate compound of the formula:

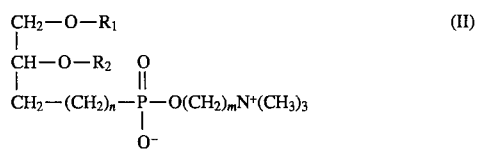

wherein $R_1$ is an alkyl group containing 12 to 20 carbon atoms, $R_2$ is a methyl group, n=0 to 14 and m=2 to 10, or enantiomer thereof, or a mixture of stereoisomers.

5. A method of treating ovarian cancer in a mammal afflicted with ovarian cancer, comprising treating the afflicted mammal with a therapeutic mount of a phosphonate compound of the formula:

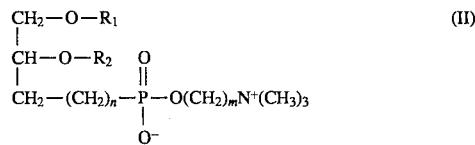

wherein $R_1$ is an alkyl group containing 12 to 20 carbon atoms, $R_2$ is a methyl group, n=0 to 14 and m=2 to 10, or enantiomer thereof, or a mixture of stereoisomers.

6. A method as claimed in claim 1 wherein $R_1$ is an alkyl group containing 18 carbon atoms and 37 hydrogen atoms, $R_2$ is a methyl group, n=0 and m=2, or enantiomer thereof, or a mixture of stereoisomers.

7. A method as claimed in claim 1 wherein $R_1$ is an alkyl group containing 18 carbon atoms and 37 hydrogen atoms, $R_2$ is a methyl group, n=1 and m=2, or enantiomer thereof, or a mixture of stereoisomers.

8. A method as claimed in claim 1 wherein $R_1$ is an alkyl group containing 16 carbon atoms and 33 hydrogen atoms, $R_2$ is a methyl group, n=0 and m=2, or enantiomer thereof, or a mixture of stereoisomers.

9. A method as claimed in claim 1 wherein $R_1$ is an alkyl group containing 16 carbon atoms and 33 hydrogen atoms, $R_2$ is a methyl group, n=1 and m=2, or enantiomer thereof, or a mixture of stereoisomers.

10. A method as claimed in claim 2 wherein $R_1$ is an alkyl group containing 18 carbon atoms and 37 hydrogen atoms, $R_2$ is a methyl group, n=0 and m=2, or enantiomer thereof, or a mixture of stereoisomers.

11. A method as claimed in claim 2 wherein $R_1$ is an alkyl group containing 18 carbon atoms and 37 hydrogen atoms, $R_2$ is a methyl group, n=1 and m=2, or enantiomer thereof, or a mixture of stereoisomers.

12. A method as claimed in claim 2 wherein $R_1$ is an alkyl group containing 16 carbon atoms and 33 hydrogen atoms, $R_2$ is a methyl group, n=0 and m=2, or enantiomer thereof, or a mixture of stereoisomers.

13. A method as claimed in claim 2 wherein $R_1$ is an alkyl group containing 16 carbon atoms and 33 hydrogen atoms, $R_2$ is a methyl group, n=0 and m=2, or enantiomer thereof, or a mixture of stereoisomers.

14. A method as claimed in claim 3 wherein $R_1$ is an alkyl group containing 18 carbon atoms and 37 hydrogen atoms, $R_2$ is a methyl group, n=0 and m=2, or enantiomer thereof, or a mixture of stereoisomers.

15. A method as claimed in claim 3 wherein $R_1$ is an alkyl group containing 18 carbon atoms and 37 hydrogen atoms, $R_2$ is a methyl group, n=1 and m=2, or enantiomer thereof, or a mixture of stereoisomers.

16. A method as claimed in claim 3 wherein $R_1$ is an alkyl group containing 16 carbon atoms and 33 hydrogen atoms, $R_2$ is a methyl group, n=0 and m=2, or enantiomer thereof, or a mixture of stereoisomers.

17. A method as claimed in claim 3 wherein $R_1$ is an alkyl group containing 16 carbon atoms and 33 hydrogen atoms, $R_2$ is a methyl group, n=1 and m=2, or enantiomer thereof, or a mixture of stereoisomers.

18. A method as claimed in claim 4 wherein $R_1$ is an alkyl group containing 18 carbon atoms and 37 hydrogen atoms, $R_2$ is a methyl group, n=0 and m=2, or enantiomer thereof, or a mixture of stereoisomers.

19. A method as claimed in claim 4 wherein $R_1$ is an alkyl group containing 18 carbon atoms and 37 hydrogen atoms, $R_2$ is a methyl group, n=1 and m=2, or enantiomer thereof, or a mixture of stereoisomers.

20. A method as claimed in claim 4 wherein $R_1$ is an alkyl group containing 16 carbon atoms and 33 hydrogen atoms, $R_2$ is a methyl group, n=0 and m=2, or enantiomer thereof, or a mixture of stereoisomers.

21. A method as claimed in claim 4 wherein $R_1$ is an alkyl group containing 16 carbon atoms and 33 hydrogen atoms, $R_2$ is a methyl group, n=1 and m=2, or enantiomer thereof, or a mixture of stereoisomers.

22. A method as claimed in claim 5 wherein $R_1$ is an alkyl group containing 18 carbon atoms and 37 hydrogen atoms, $R_2$ is a methyl group, n=0 and m=2, or enantiomer thereof, or a mixture of stereoisomers.

23. A method as claimed in claim 5 wherein $R_1$ is an alkyl group containing 18 carbon atoms and 37 hydrogen atoms, $R_2$ is a methyl group, n=1 and m=2, or enantiomer thereof, or a mixture of stereoisomers.

24. A method as claimed in claim 5 wherein $R_1$ is an alkyl group containing 16 carbon atoms and 33 hydrogen atoms, $R_2$ is a methyl group, n=0 and m=2, or enantiomer thereof, or a mixture of stereoisomers.

25. A method as claimed in claim 5 wherein $R_1$ is an alkyl group containing 16 carbon atoms and 33 hydrogen atoms, $R_2$ is a methyl group, n=1 and m=2, or enantiomer thereof, or a mixture of stereoisomers.

26. A method as claimed in claims 1 wherein the phosphonate compound includes either of the opposite stereochemical configurations or a mixture thereof.

27. A method as claimed in claims 1 wherein the phosphonate compound, or a pharmaceutically acceptable acid or salt thereof, is administered orally, intravenously, intramuscularly, intradermally, subcutaneously, topically or intravenously in the form of a liposome, with or without a pharmaceutically acceptable carrier.

28. A method as claimed in claim 2 wherein the phosphonate compound, or a pharmaceutically acceptable acid or salt thereof, is administrated orally, intravenously, intramuscularly, intradermally, subcutaneously, topically, or intravenously in the form of a liposome, with or without a pharmaceutically acceptable carrier.

29. A method as claimed in claim 3 wherein the phosphonate compound, or a pharmaceutically acceptable acid or salt thereof, is administrated orally, intravenously, intramuscularly, intradermally, subcutaneously, topically, or intravenously in the form of a liposome, with or without a pharmaceutically acceptable carrier.

30. A method as claimed in claim 4 wherein the phosphonate compound, or a pharmaceutically acceptable acid or salt thereof, is administrated orally, intravenously, intramuscularly, intradermally, subcutaneously, topically, or intravenously in the form of a liposome, with or without a pharmaceutically acceptable carrier.

31. A method as claimed in claim 5 wherein the phosphonate compound, or a pharmaceutically acceptable acid or salt thereof, is administrated orally, intravenously, intramuscularly, intradermally, subcutaneously, topically, or intravenously in the form of a liposome, with or without a pharmaceutically acceptable carrier.

32. A method as claimed in claim 6 wherein the phosphonate compound, or a pharmaceutically acceptable acid or salt thereof, is administrated orally, intravenously, intramuscularly, intradermally, subcutaneously, topically, or intravenously in the form of a liposome, with or without a pharmaceutically acceptable carrier.

33. A method as claimed in claim 7 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

34. A method as claimed in claim 8 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

35. A method as claimed in claim 9 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

36. A method as claimed in claim 10 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

37. A method as claimed in claim 11 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

38. A method as claimed in claim 12 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

39. A method as claimed in claim 13 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

40. A method as claimed in claim 14 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

41. A method as claimed in claim 15 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

42. A method as claimed in claim 16 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

43. A method as claimed in claim 17 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

44. A method as claimed in claim 18 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

45. A method as claimed in claim 19 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

46. A method as claimed in claim 20 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

47. A method as claimed in claim 21 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

48. A method as claimed in claim 22 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

49. A method as claimed in claim 23 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

50. A method as claimed in claim 24 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

51. A method as claimed in claim 25 wherein the phosphonate compound, or a pharmaceutically acceptable acid or salt thereof, is administered orally, intravenously, intramuscularly, intradermally, subcutaneously, topically, or intravenously in the form of a liposome, with or without a pharmaceutically acceptable carrier.

* * * * *